US00PP12265P2

(12) United States Plant Patent
Masuda

(10) Patent No.: US PP12,265 P2
(45) Date of Patent: Dec. 11, 2001

(54) TIBOUCHINA PLANT NAMED 'ANGYO WHITE'

(75) Inventor: Tamotsu Masuda, Kawaguchi (JP)

(73) Assignee: Hines Nurseries, Inc., Irvine, CA (US)

( * ) Notice: Subject to any disclaimer, the term of this patent is extended or adjusted under 35 U.S.C. 154(b) by 0 days.

(21) Appl. No.: 09/460,000

(22) Filed: Dec. 13, 1999

(51) Int. Cl.[7] ..... A01H 5/00

(52) U.S. Cl. ..... Plt./226

(58) Field of Search ..... Plt./226

*Primary Examiner*—Bruce R. Campell
*Assistant Examiner*—Michelle Kizilkaya
(74) *Attorney, Agent, or Firm*—C. A. Whealy

(57) ABSTRACT

A distinct cultivar of Tibouchina plant named 'Angyo White', characterized by its upright, somewhat outwardly spreading and open plant habit; large white flowers; and dark green leaves.

1 Drawing Sheet

BACKGROUND OF THE INVENTION

The present invention relates to a new and distinct cultivar of Tibouchina plant, botanically known as *Tibouchina urvilleana*, and hereinafter referred to by the cultivar name Angyo White.

The new Tibouchina is a product of a planned breeding program conducted by the Inventor in Kawaguchi City, Japan. The objective of the breeding program was to create compact Tibouchina cultivars with unique flower colors.

The new Tibouchina originated from a cross made by the Inventor of two unidentified selections of *Tibouchina urvilleana*. The cultivar Angyo White was discovered and selected by the Inventor as a flowering plant within the progeny of the stated cross in a controlled environment in Kawaguchi City, Japan. Plants of the new Tibouchina differ from the parent selections primarily in flower color.

Asexual reproduction of the new cultivar by terminal cuttings taken at Irvine, Calif., since 1997 has shown that the unique features of this new Tibouchina are stable and reproduced true to type in successive generations.

SUMMARY OF THE INVENTION

Plants of the cultivar Angyo White have not been observed under all possible environmental conditions. The phenotype may vary somewhat with variations in environment such as temperature, light intensity, daylength, and fertility level without, however, any variance in genotype.

The following traits have been repeatedly observed and are determined to be the unique characteristics of 'Angyo White'. These characteristics in combination distinguish 'Angyo White' as a new and distinct cultivar:

1. Upright, somewhat outwardly spreading and open plant habit.
2. Large white flowers.
3. Dark green leaves.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which more accurately describe the actual colors.

The photograph at the top of the sheet comprises a side perspective view of a typical plant of the new Tibouchina.

The photograph at the bottom of the sheet comprises a close-up view of typical open flowers, typical flower buds and hypanthium, and typical young and mature leaves of the new Tibouchina.

DETAILED BOTANICAL DESCRIPTION

In the following description, color references are made to The Royal Horticultural Society Colour Chart except where general terms of ordinary dictionary significance are used.

Plants used for the description and photographs were about 18 months old from rooted cuttings and were grown under outdoor production conditions during the spring and early summer in Irvine, Calif.

Botanical classification: *Tibouchina urvilleana* cultivar Angyo White.

Parentage:
- *Female parent.*—Unidentified selection of *Tibouchina urvilleana.*
- *Male parent.*—Unidentified selection of *Tibouchina urvilleana.*

Propagation:
- *Type.*—By stem cuttings.
- *Time to initiate roots.*—About 14 days at 22° C.
- *Time to develop roots* (*time to produce a rooted liner*) .—About 42 days at 22° C.
- *Root appearance.*—Fibrous, freely branching.

Plant description:
- *Crop time.*—From cuttings, about 18 months are required to produce a flowering plant in a five-gallon container.
- *Form.*—Upright, somewhat outwardly spreading and open habit; subshrub.
- *Plant height.*—About 55 cm.
- *Plant width.*—About 60 cm.
- *Vigor.*—Low.
- *Lateral branches.— Quantity: Freely branching; pinching enhances lateral branch development. Length: Primary laterals, about* 27 cm; secondary laterals, about 20 cm. Diameter: About 5.5 mm. Internode length: About 6 cm. Texture: Scabrous; irregular tiny scale-like hairs. Color: Older stems, 177A to 177B; semi-woody stems, 144A; young stems, 144B.

*Foliage description.*—Leaves simple, generally symmetrical, opposite. Quantity per lateral branch: About 15. Length: About 8.5 cm. Width: About 4 cm. Shape: Elliptic. Apex: Acute. Base: Attenuate. Margin: Entire. Texture: Coarse, grainy; both surfaces pubescent. Color: Young foliage, upper surface: 146A. Young foliage, lower surface: 146C. Mature foliage, upper surface: 147A. Mature foliage: lower surface: 147B to 147C. Venation, upper surface: 147B. Venation, lower surface: 146C. Petiole: Length: About 1.6 cm. Diameter: About 2 mm. Color: 146D.

Flower description:

*Flower type and habit.*—Rounded flowers arranged in terminal panicles, typically three flowers per terminal; flowers face outward or upright. Corolla with five to seven petals in a single radial whorl. Individual flowers last about two days on the plant. Flowers persistent.

*Natural flowering season.*—Summer through fall.

*Fragrance.*—None detected.

*Flower buds.*—Length: About 3.5 cm. Diameter: About 1.3 cm. Shape: Ovoid. Color: 144D.

*Flowers size.*—Diameter: About 7 cm. Depth: About 3.25 cm.

*Petals.*—Quantity: About five. Length (beyond throat): About 3.5 cm. Width: Apex, about 2.5 cm; base, about 5 mm. Shape: Spatulate. Apex: Rounded. Aspect: Concave towards base, reflexed towards apex. Margin: Entire. Texture: Smooth, satiny. Color: When opening and fully opened, upper and lower surface: 155D.

*Calyx.*—Calyx length: About 2.5 cm. Calyx diameter: About 9 mm. Shape: Hypanthium; separated sepals, elliptic. Sepal quantity: Five. Sepal apex: Acute. Sepal margin: Entire. Sepal color: Upper surface, 144C; lower surface, 144D.

*Pedicel.*—Strength: Strong. Angle: Upright to about 30° to vertical. Length: About 1.6 cm. Color: 145B.

*Reproductive organs.*—Androecium: Stamen number: About ten. Anther shape: Linear. Anther size: About 1.2 cm by 1.75 mm. Anther color: 145B. Pollen: None observed. Gynoecium: Pistil number: One with five locules. Pistil length: About 3 cm. Stigma color: 137B. Style length: About 2.5 cm. Style color: 145D. Ovary color: 145D.

*Seed development.*—Seed development has not been observed.

Disease resistance: Under commercial conditions, resistance to pathogens common to *Tibouchina urvilleana* has been observed.

It is claimed:

1. A new and distinct cutlivar of Tibouchina plant named 'Angyo White', as illustrated and described.

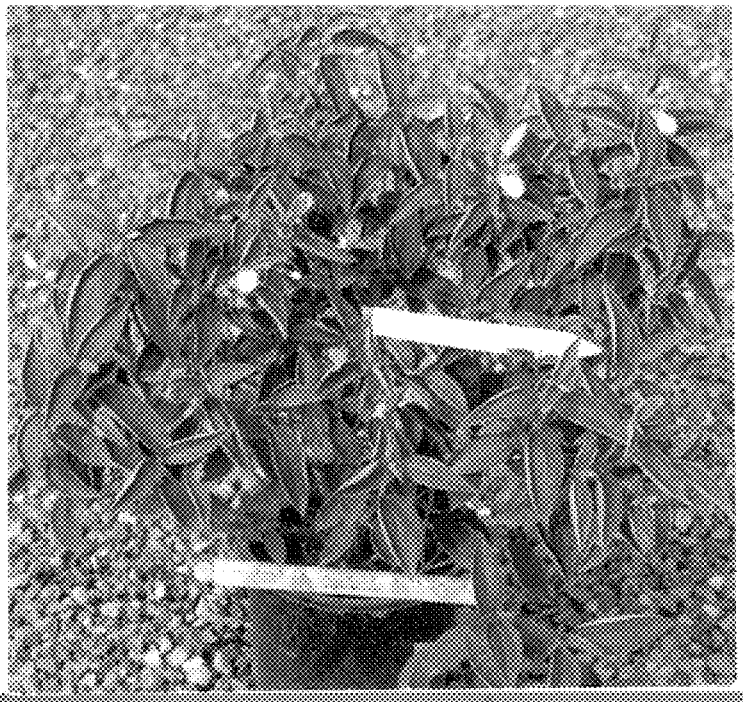
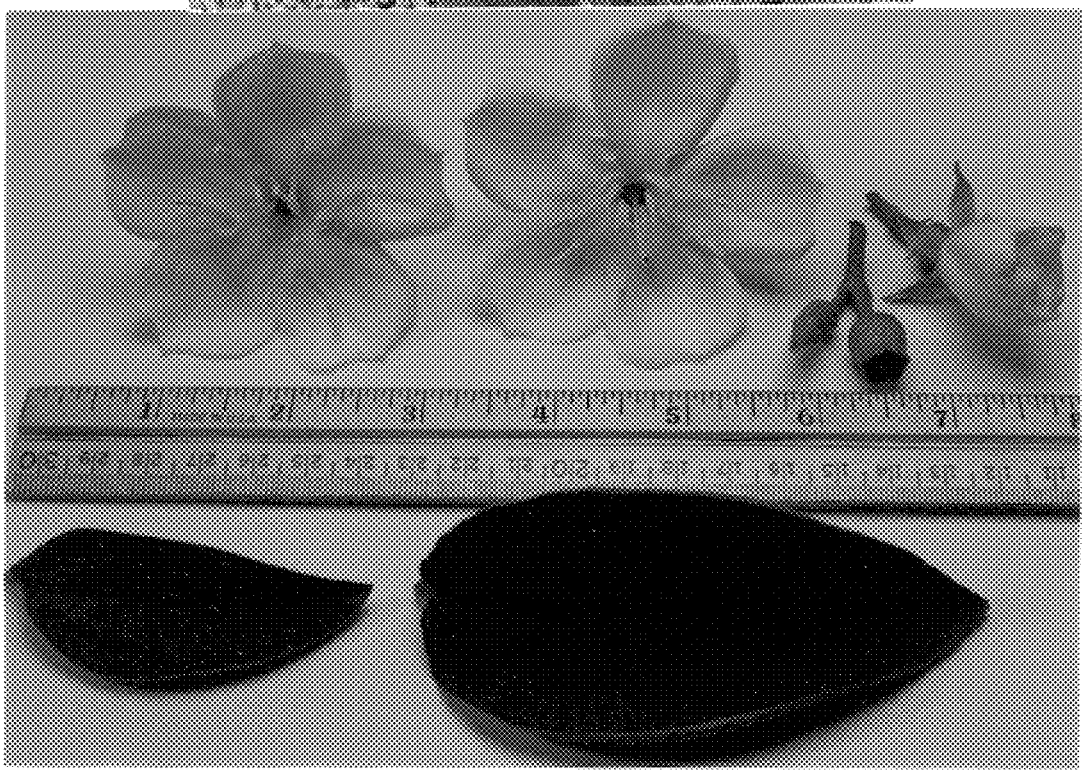

* * * * *